(12) United States Patent
Giossi et al.

(10) Patent No.: US 8,357,657 B2
(45) Date of Patent: Jan. 22, 2013

(54) THERAPEUTIC COMBINATION COMPRISING A PULMONARY SURFACTANT AND A STEROID

(75) Inventors: Massimo Giossi, Parma (IT); Roberta Razzetti, Parma (IT); Paolo Chiesi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 259 days.

(21) Appl. No.: 12/786,845

(22) Filed: May 25, 2010

(65) Prior Publication Data

US 2011/0130333 A1    Jun. 2, 2011

(30) Foreign Application Priority Data

May 25, 2009 (EP) .................................... 09161001

(51) Int. Cl.
*A61K 38/00* (2006.01)
*C07K 14/785* (2006.01)

(52) U.S. Cl. ...................................... 514/15.5
(58) Field of Classification Search .................. None
See application file for complete search history.

(56) References Cited

U.S. PATENT DOCUMENTS

2008/0269221 A1    10/2008 Andersen et al.

FOREIGN PATENT DOCUMENTS

| EP | 1452 179 A1 | * | 9/2004 |
| EP | 1 683 514 A1 | * | 7/2006 |
| WO | 2005/021037 | | 3/2005 |

OTHER PUBLICATIONS

Sinha et al. A multicenter, randomized, controlled trial of lucinactant versus poractant alfa among very premature infants at high risk for respiratory distress syndrome. Pediatrics, 2005, vol. 115, No. 4, pp. 1030-1038.*
LaForce et al. Controlled trial of beclomethasone dipropionate by nebulization in oxygen- and ventilator-dependent infants. J Pediatr, 1993, vol. 122, No. 2, pp. 285-288.*
Muratore et al. Prevention with clodronate of osteoporosis secondary to inhaled corticosteroid treatment in patients with chronic asthmatic bronchitis. Int J Clin Pharmacol Res, 2000, vol. 20, Nos. 3-4, pp. 61-64.*

* cited by examiner

*Primary Examiner* — Marcela M Cordero Garcia
(74) *Attorney, Agent, or Firm* — Oblon, Spivak, McClelland, Maier & Neustadt, L.L.P.

(57) ABSTRACT

Administration of a modified natural surfactant in combination with a corticosteroid is effective for the prevention of bronchopulmonary dysplasia (BPD) and lowers the markers of pulmonary oxidative stress.

20 Claims, No Drawings

THERAPEUTIC COMBINATION COMPRISING A PULMONARY SURFACTANT AND A STEROID

CROSS REFERENCES TO RELATED APPLICATIONS

This application claims priority to European Patent Application No. 09161001.4, filed on May 25, 2009, which is incorporated herein by reference in its entirety.

BACKGROUND OF THE INVENTION

1. Field of the Invention

The present invention relates to compositions for the treatment of preterm infants. In particular the present invention relates to pulmonary surfactant compositions which are useful for reducing the pulmonary oxidative damage and the risk of developing bronchopulmonary dysplasia in preterm infants. The present invention further relates to methods for treating and/or preventing certain conditions by administering such a pulmonary surfactant composition.

2. Discussion of the Background

The human lung is composed of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

The lung surfactant complex is composed primarily of lipid and contains minor amounts of various proteins. An absence of adequate levels of this complex results in malfunction of the lungs. This syndrome is called Respiratory Distress Syndrome (RDS) and it commonly affects preterm infants.

The mainstay of the treatment of RDS is replacement therapy with exogenous pulmonary surfactant preparations extracted from animal lungs, known as modified natural surfactants. For instance, modified natural surfactants used in the clinical practice are poractant alfa derived from porcine lung, and sold under the trademark of CUROSURF®, beractant (SURFACTEN® or SURVANTA®) and bovactant (ALVEOFACT®), both derived from bovine lung, and calfactant derived form calf lung (INFASURF®).

Exogenous pulmonary surfactants are currently administered by endotracheal instillation as a suspension in a saline aqueous solution to intubated pre-term infants kept under mechanical ventilation with oxygen.

Although said therapy has greatly increased postnatal survival, children that survive RDS have a high risk of developing bronchopulmonary dysplasia (BPD), a complication that impedes lung development and ultimately leads to impaired breathing. Evidence indicates that pulmonary inflammation and oxidative injury of lung tissues play an important role in the pathogenesis of BPD. Furthermore, inflammation and oxidative stress contribute to surfactant inactivation through the alveolar transudation of plasma proteins and cells and the direct action of free radicals.

The risk of developing BPD in infants affected by RDS can be reduced by administering a corticosteroid within a few weeks postnatally. However, the effectiveness of postnatal corticosteroid administration is offset by possible adverse systemic effects, e.g., hypertension, hyperglycemia, gastrointestinal complications, and neurodevelopmental disability.

As an alternative to systemic administration, delivery of corticosteroid by inhalation or intracheal instillation has been proposed. For example, Yeh et al. (Pediatrics 2008, 121(5), e1310-e1318) proposed the intratracheal instillation of budesonide using the surfactant Survanta® as a carrier. However, as reported in US 2007/0225233, the relevant delivery procedure suffers from some drawbacks in terms of compliance as it foresees the administration of the medicament in four aliquots, each aliquot being administered in different and rather complicated positions of the infant.

In view of the above considerations, there is still a need to develop a more compliant medicament able of effectively reducing the markers of pulmonary inflammation and oxidative stress, and hence the risk of BPD in infants suffering from RDS.

In particular, since mechanical ventilation is an invasive procedure which has been recognized to contribute to the development of BPD, it would be of particular advantage to provide a medicament that may also be effectively administered by methods avoiding said respiratory support.

SUMMARY OF THE INVENTION

Accordingly, it is one object of the present invention to provide novel compositions which are useful for treating infants suffering from RDS.

It is another object of the present invention to provide novel compositions which are useful for treating infants suffering from RDS and which reduce the risk of the infant developing BPD.

It is another object of the present invention to provide novel compositions which are useful for treating infants suffering from RDS and which effectively reduce the markers of pulmonary inflammation and oxidative stress, and hence the risk of BPD in the infants.

It is another object of the present invention to provide novel compositions which are useful for treating infants suffering from RDS and which effectively reduce the markers of pulmonary inflammation and oxidative stress, and hence the risk of BPD in the infants, and which are effectively administered without respiratory support.

It is another object of the present invention to provide novel methods for treating infants suffering from RDS.

It is another object of the present invention to provide novel methods for treating infants suffering from RDS and which reduce the risk of the infant developing BPD.

It is another object of the present invention to provide novel methods for treating infants suffering from RDS and which effectively reduce the markers of pulmonary inflammation and oxidative stress, and hence the risk of BPD in the infants.

It is another object of the present invention to provide novel methods for treating infants suffering from RDS and which effectively reduce the markers of pulmonary inflammation and oxidative stress, and hence the risk of BPD in the infants, and which involve effective administration without respiratory support.

These and other objects, which will become apparent during the following detailed description, have been achieved by the inventors' discovery that administering poractant alfa and beclometasone dipropionate is useful for treating RDS and preventing BPD).

Thus, the present invention provides compositions which comprise poractant alfa at a dose of 100 to 200 mg/kg in combination with beclometasone dipropionate at a dose equal to or higher than 0.4 mg/kg.

The present invention also provides the use of poractant alfa at a dose of 100 to 200 mg/kg in combination with beclometasone dipropionate at a dose equal to or higher than 0.4 mg/kg for the manufacture of a medicament for the prevention of bronchopulmonary dysplasia (BPD).

Preferably, said use lowers the markers of pulmonary oxidative stress.

Preferably, beclometasone dipropionate is used at a dose of 0.8 mg/kg.

The present invention also provides a combination of:

(a) poractant alfa at a dose comprised between 100 and 200 mg/kg; and (b) beclometasone dipropionate at a dose equal to or higher than 0.4 mg/kg, preferably of 0.8 mg/kg, for simultaneous, sequential or separate administration for the prevention of bronchopulmonary dysplasia (BPD), preferably for simultaneous administration.

The invention also provides a medicament comprising a fixed combination of poractant alfa at a dose of 100 to 200 mg/kg with beclometasone dipropionate at a dose equal to or higher than 0.4 mg/kg, preferably of 0.8 mg/kg.

In a particular embodiment, said medicament is in form of pharmaceutical composition for inhalation or intratracheal administration comprising said fixed combination.

In another embodiment, the invention provides a kit comprising:

(a) poractant alfa at a dose of 100 to 200 mg/kg and a pharmaceutically acceptable carrier or diluent in a first unit dosage form;

(b) beclometasone dipropionate at a dose equal to or higher than 0.4 mg/kg, preferably of 0.8 mg/kg and a pharmaceutically acceptable carrier or diluent in a second unit dosage form; and (c) a container which containing said first and second dosage forms.

In a further embodiment, the invention provides a method for the prevention of bronchopulmonary dysplasia, comprising the administration to a patient in need of such treatment poractant alfa at a dose of 100 and 200 mg/kg and beclometasone dipropionate at a dose equal to or higher than 0.4 mg/kg, preferably of 0.8 mg/kg.

DETAILED DESCRIPTION OF THE PREFERRED EMBODIMENTS

As used herein the term "bronchopulmonary dysplasia (BPD)" refers to a chronic pulmonary disorder, also known as chronic lung disease (CLD), which is the consequence of unresolved or abnormally repaired lung damage.

BPD typically occurs in very low birth weight (VLBW) infants who sustain lung damage as a result of oxygen toxicity and barotrauma from mechanical ventilation early in life.

As used herein the term "modified natural surfactant" refers to a lipid extract of minced mammalian lung. Due to the lipid extraction process used in the manufacture process, the hydrophilic proteins SP-A and SP-D are lost. These preparations have variable amounts of two hydrophobic, surfactant-associated proteins SP-B and SP-C and, depending on the method of extraction, may contain non-surfactant lipids, proteins or other components.

As used herein the term "poractant alfa" refers to a modified natural surfactant extracted from porcine lungs substantially consisting of polar lipids, mainly phospholipids and the proteins, SP-B and SP-C. Poractant alfa is available under the trademark CUROSURF®. Poractant alfa belongs to the class of surfactants which are extracts of minced mammalian lung, essentially containing polar lipids, mainly phospholipids, and the surfactant proteins SP-B and SP-C.

As used herein the term "fixed combination" means a combination wherein the active substances are in a fixed quantitative ratio.

"Pharmaceutical acceptable" is a term used herein that refers to a medium that does not produce an allergic or similar untoward reaction when administered to an infant.

"Surfactant activity" for a surfactant preparation is defined as the ability to lower the surface tension.

The in vitro efficacy of exogenous surfactant preparations is commonly tested by measuring their capability of lowering the surface tension using suitable apparatus such as Wilhelmy Balance, Pulsating Bubble Surfactometer, Captive Bubble Surfactometer, and Capillary Surfactometer.

The in vivo efficacy of exogenous surfactant preparations is tested by measuring lung mechanics in pre-term animal models according to methods known to the skilled person in the art.

As used herein, the term "severe RDS" indicates a form of infant respiratory distress syndrome inversely related to the gestational age and/or birthweight which can be diagnosed clinically and/or radiographically according to methods known by the skilled person in the art.

Since it is general knowledge that the effect of acute administration of a corticosteroid on lung mechanics is negligible, in the context of the present application, the term "synergistic" means that the activity of the surfactant plus that of beclometasone dipropionate is more than would be expected by that of the surfactant only on any one of the lung mechanics parameters.

The present invention is based in part on the unexpected finding that beclometasone dipropionate at a dose equal to or higher than 0.4 mg/kg can be combined with a modified natural surfactant such as poractant alfa to effectively reducing the risk of bronchopulmonary dysplasia (BPD) without altering the surface activity of the surfactant.

Therefore, the present invention is directed to poractant alfa at a dose of 100 to 200 mg/kg in combination with beclometasone dipropionate at a dose equal to or higher than 0.4 mg/kg as a medicament for the prevention of bronchopulmonary dysplasia (BPD).

Advantageously, the dose of beclometasone dipropionate is higher than 0.4 mg/kg (400 µg/kg), preferably in the range of 0.6 to 0.8 µg/kg.

In one embodiment, the dose of beclometasone dipropionate is 0.6 mg/kg.

The preferred dose of beclometasone dipropionate is 0.8 mg/kg (800 µg/kg).

Preferably, the dose of poractant alfa is 200 mg/kg.

The combination of poractant alfa and beclometasone dipropionate at the claimed doses may be administered sequentially separately or together. Advantageously, when the two active substances are administered together, they are administered as a fixed combination.

Therefore, the present invention also concerns a medicament comprising the two active substances at the claimed doses as a fixed combination. The medicament may be in form of pharmaceutical composition.

Said formulations may be administered in the form of a solution, dispersion, suspension or dry powder. Preferably, said compositions comprise the claimed combination suspended in a suitable physiologically tolerable solvent.

More preferably, the formulation comprises an aqueous solution, preferably sterile, which may also comprise pH buffering agents and other pharmaceutically acceptable excipients such as polysorbate 20, polysorbate 80, or sorbitan monolaurate as wetting agents and sodium chloride as isotonicity agent.

The formulations may be distributed in unit-dose or multi-dose containers, for example sealed ampoules and vials, or may be stored in a frozen or freeze-dried (lyophilized) condition requiring only the addition of sterile liquid carrier immediately prior to use.

Preferably, the formulation is supplied as sterile suspension in a buffered physiological saline (0.9% w/v sodium chloride) aqueous solution in single-use vials.

The administration of the claimed formulation may be carried out according to known methods, e.g. by endotracheal instillation, by spray administration, or nebulisation by jet ultrasonic, or mesh-vibrating nebulisers commonly available on the market.

When the formulation is administered by endotracheal instillation, depending on the severity of the respiratory distress syndrome, different methods can be appropriate. For example the claimed formulation may be administered by endotracheal instillation to pre-term infants kept under continuous or intermittent positive pressure ventilation.

Alternatively, the formulation may be administered by the use of a thin catheter placed in the trachea and the patient respiration supported through specially designed nasal devices such as masks, prongs or tubes according to methodology known as nasal Continuous Positive Airway Pressure (nCPAP), according to the procedure described in WO 2008/148469.

The latter approach would be only possible with an exogenous surfactant such as poractant alfa having a low viscosity, as a high viscosity would make the passage of the surfactant through the thin catheter more difficult.

The volume of the aqueous solution in which the two combined active substances are suspended will depend on the desired concentration.

Advantageously, the volume of the formulation should be not more than 5.0 ml, preferably 4.5 to 2.0 ml, more preferably 3.5 to 2.5 ml.

For example, for an amount of poractant alfa of 200 mg and of beclometasone dipropionate of 0.8 mg, when a 2.5 ml volume is used, the final concentrations of poractant alfa and beclometasone dipropionate would be 80 mg/ml and 0.32 mg/ml, respectively.

If a volume of 4.5 ml were to be used, for the same doses the final concentrations would be about 44 mg/ml and about 0.18 mg/ml, respectively.

If a dose of poractant alfa of 100 mg were to be used, for a volume of 2.5 ml, the final concentrations would be 40 mg/ml and 0.32 mg/ml, respectively.

In other embodiment, when poractant alfa and beclometasone dipropionate are administered separately, the individual active substances can be formulated separately. In this case, the two individual active substances do not unconditionally have to be taken at the same time.

In the case of such a separate administration, the formulation of the two individual active substances can be packed at the same time in a suitable container mean. Such separate packaging of the components in a suitable container mean is also described as a kit.

Therefore, this invention is also directed to a kit, comprising:

(a) an amount of poractant alfa of 100 to 200 mg and a pharmaceutically acceptable carrier or diluent in a first unit dosage form;

(b) an amount of beclometasone dipropionate equal to or higher than 0.4 mg and a pharmaceutically acceptable carrier or diluent in a second unit dosage form; and (c) a container which contains said first and second dosage forms.

Preferably, the first unit dosage form is a single-use vial filled with 2.5 ml of a sterile formulation of 80 mg/ml poractant alfa suspended in a buffered physiological saline (0.9% w/v sodium chloride) aqueous solution, while the second unit dosage form is a single-use vial filled with 2 ml of a sterile formulation of 0.8 mg/ml micronised beclometasone dipropionate suspended in an aqueous solution comprising polysorbate (Tween) 20, sorbitan monolaurate and sodium chloride. The container may be any which is suitable for container the two dosage units, such as a paper or cardboard box or a plastic or foil pouch.

The combination of the invention which can be administered to the infant after birth according to conditions which shall be established by the skilled person in the art, is suitable to prevent, delay, alleviate, arrest or inhibit development of bronchopulmonary dysplasia.

Preferably, the combination of the invention is suitable to prevent development of bronchopulmonary dysplasia in preterm infants affected by a severe form of respiratory distress syndrome (RDS).

However, it might also be used for the prophylaxis and/or treatment of other diseases related to the lack or dysfunction of the endogenous surfactant such as respiratory distress syndrome in adults (ARDS), acute lung injury (ALI), and meconium aspiration syndrome (MAS).

The advantages of combining poractant alfa with a dose of beclometasone dipropionate higher than that currently applied in therapeutic practice will be apparent from the following findings.

It has indeed been found, in a randomized study in preterm lambs with RDS, that poractant alfa in combination with a dose of beclometasone dipropionate higher than 0.4 mg/kg acts in an additive way on some lung tissue oxidative stress markers and in a synergistic way on a lung mechanics parameter.

The study was carried out by intratracheal administration of poractant alfa plus beclometasone dipropionate at different doses in comparison to the sole surfactant.

Lung tissue oxidation was studied by measuring total hydroperoxides (TH), advanced oxidation protein products (AOPP), and non protein bound iron (NPBI) in bronchial aspirate samples. TH was lower in the groups treated with surfactant plus 400 or 800 µg/kg of beclometasone dipropionate than in the surfactant group, while AOPP was lower in the group treated with surfactant plus 800 µg/kg of beclometasone dipropionate than in the other groups; NPBI was similar in all groups. Lung compliance was evaluated as well.

Surfactant treatment was followed by a sustained improvement of the tidal volume (TV) and airway resistance (Raw) which, as expected, was not altered by the presence of beclometasone dipropionate, even at the highest dose. However, surprisingly, the addition of beclometasone dipropionate at a dose of 800 µg/kg resulted in a synergistic decrease of the mean airway pressure (MAP) needed to obtain the same value of TV. In contrast, in the group treated with surfactant plus beclometasone dipropionate at a dose of 400 mg/kg, the effect on MAP was statistically not different from that of the group treated with the surfactant only.

This means that softer mechanical ventilation could be applied to the patients receiving the combination of the invention with lesser risk of barotrauma.

Therefore, in view of the aforementioned findings, i.e. a reduction of the oxidative lung stress and a synergistic improvement of one of the lung mechanics parameters, the present invention provides a combination particularly efficacious for the prevention of bronchopulmonary dysplasia, Furthermore, the fact that beclometasone dipropionate is a highly lipophilic corticosteroid might favor its mucosal absorption and uptake across phospholipid cell membranes with a negligible systemic absorption, making the combination safe for therapeutic use in infants.

Other features of the invention will become apparent in the course of the following descriptions of exemplary embodiments which are given for illustration of the invention and are not intended to be limiting thereof.

EXAMPLES

Example 1

In Vitro Evaluation of the Surface Activity of Poractant Alfa in the Presence of Beclometasone Dipropionate by Capillary Surfactometer The surface activity of poractant alfa (in the presence of beclometasone dipropionate, 2 ml, 0.8 mg) is evaluated in comparison to poractant alfa alone by a capillary surfactometer commercially available from Calmia Medical, Inc., USA.

Two samples are prepared: one from a vial of poractant alfa (1.5 ml, 80 mg/ml) by diluting with saline to a concentration 1 mg/ml in phospholipids, and the other from a vial of poractant alfa (1.5 ml, 80 mg/ml) mixed with a vial of beclometasone dipropionate (2 ml, 0.8 mg) and diluted with saline to the same concentration (1 mg/ml phospholipids). A 0.5 ml sample of both solutions is then assessed in the Capillary Surfactometer.

The principle of the capillary surfactometer is to simulate terminal human airways. The sample is introduced into the narrow section of a glass capillary, where the inner diameter is 0.25 mm, similar to that of a terminal human airway. At one end the capillary is connected to a bellows and a pressure transducer. When the bellows is slowly compressed, pressure is raised and recorded. The increasing pressure causes the sample to be extruded from the narrow section of the capillary. As air gets through, pressure is abruptly lowered. If the sample contains well functioning pulmonary surfactant the sample liquid will not return to the narrow section. The steady airflow obtained by the continuous compression of the bellows will meet no resistance and the pressure recorded will be zero. If on the other hand the sample does not contain a well functioning pulmonary surfactant, the sample liquid will return repeatedly.

The behavior of poractant alfa plus beclometasone dipropionate turns out to be statistically indistinguishable from that of poractant alfa alone, indicating that beclometasone dipropionate at said dose does not affect the surface activity of the surfactant.

Example 2

In vivo Evaluation of Poractant Alfa Combined with Beclometasone Dopropionate

Materials and Methods.
Animals and Instrumentation.

All animals are delivered by Cesarean section at 124±1.7 days of gestational age from Massa ewes (term 145 days of gestational age). After exposure of the fetal head and neck, a carotid artery catheter is inserted for continuous blood pressure monitoring and blood sampling; the catheter is connected to pressure transducers, zero-referenced to mid-chest level.

A venous catheter is inserted in the right internal jugular vein for continuous infusion of fluids (dextrose 10%, 100 ml/kg/d) and medications and an endotracheal tube is tied into the trachea. The fetal lung fluid that could be easily aspirated by syringe is recovered, and the lambs are delivered and weighed (2425±410 grams). A standard limb lead electrocardiogram (ECG) is used. Rectal temperature is kept within a normal range using electric warming pads.

Before the first breath the lambs receive randomly 200 mg/kg of poractant alfa (CUROSURF®, Chiesi SpA, Parma, Italy), followed by 10 ml air given into the airways by syringe, or 200 mg/kg of the same surfactant combined with 400 or 800 µg/kg of beclometasone dipropionate (CLENIL A®, Chiesi SpA, Parma, Italy). Randomization is performed using the closed envelope methods before the delivery.

All animals are ventilated for 6 hours with time-cycled and pressure-limited infant ventilators (Newport Breeze Ventilator, Soma Technology Inc., Bloomfield, Conn., USA) using similar ventilation strategies. Rate of 60 breaths/min, inspiratory time of 0.5 seconds, and positive end-expiratory pressure (PEEP) of 4 cm $H_2O$ are not changed. Peak inspiratory pressure (PIP) is changed to maintain $pCO_2$ at 35-65 torr. Pressure was limited to PIP 35 cm $H_2O$ to avoid pneumothorax. Fraction of inspired oxygen is adjusted to keep a target $pO_2$ of 100-150 mm Hg. To exclude the possibility that changes in ventilator setting affect the results of the study, persons responsible for ventilator adjustments are masked to the treatment assignment.

Blood gas, pH, and base excess (BE) are analyzed by a blood gas, electrolyte, and metabolite system (Radiometer Copenhagen USA, West Lake, Ohio) at least every 30 minutes or when ventilatory status changed as indicated by changes in chest movement and tidal volumes.

During the whole experiment the plasma expander polygeline (EMAGEL®, Novaselect, Potenza, Italy) and/or dopamine, 10-20 µg/kg/min are administered as needed to maintain a mean SAP above 30 mmHg. Metabolic acidosis (pH <7.25 and BE <8 mmol/L) is corrected with sodium bicarbonate or THAM infusion (in case of hypercapnia: $PaCO_2$>45 mmHg). The pH, $pO_2$, and $pCO_2$ of each animal are recorded at least as soon as possible after delivery, and after 1 ($T_1$), 2 ($T_2$), 4 ($T_4$), and 6 ($T_6$) hours from surfactant administration.

Lung Mechanics Monitoring.

Mean airway pressure (MAP), dynamic lung compliance (Cdyn), exhaled tidal volume (TV), and expiratory resistance (Raw) are measured with a neonatal respiratory monitor (Florian Neonatal Respiration Monitor™, Acutronic, Hirzel, Switzerland) and their values at baseline, $T_1$, $T_2$, $T_4$, and $T_6$ are recorded.

Lung Oxidative Stress Assays.

Bronchial aspirate samples from animals in each groups were obtained with the following technique: 1 ml/kg sterile 0.9% saline was instilled using a 10 ml syringe through a 8F gauge feeding catheter that was placed in the endotracheal tube so that the tip extends 2 cm beyond the distal end of the tube. The saline was instilled and immediately aspirated back into the syringe.

The mean volume of saline returned is 1.5 ml. All samples were clarified by centrifugation (1000 rpm×5 min) and the supernatant was immediately frozen at −70° C. and stored for subsequent analysis. Bronchial aspirate samples were collected from each animal before surfactant administration, after exposure of the fetal head, and at 1 ($T_1$), 2 ($T_2$), 4 ($T_4$), and 6 ($T_6$) hours from surfactant administration.

In each bronchial aspirate sample, the total hydroperoxides (TH) concentration, the advanced oxidation protein products (AOPP), and the non-protein bound iron (NPBI) were measured. TH production was measured with a d-ROMs Kit (Diacron srl, Italy) by using a spectrophotometric procedure.

The results are expressed in conventional units (Carr units: the value of 1 Can unit is equal to a concentration of 0.08 mg/dl of hydrogen peroxide). AOPP is measured by the method reported by Witko-Sarsat et al. (Kidney Int. 1996, 49(5):1304-13), using spectrophotometry on a microplate reader. The AOPP concentration is expressed as µmol/l chloramine-T equivalents. NPBI levels are determined by HPLC using the method described by Kime et al. (Clin Sci (Lond) 1996, 91(5):633-8), partially modified. The results are expressed in nmol/ml.

Tissue Removal and Pathologic Examination.

At the end of the experiment, the animals were killed with an overdose of pentobarbital. The thorax was carefully opened to check for signs of pneumothorax and to harvest tissue. The trachea and lungs were removed and put in a buffered 10% formalin bath. Two random pulmonary specimens were obtained from the upper and the lower lobes of both lungs. Routine techniques were used to prepare the tissues for paraffin embedding. Five-micrometer thick sections were stained with hematoxylin-eosin and two pathologists performed the blinded microscopic examination. Terminal airways distension was graded as 0 when it was found similar to that of the control lungs, 1 when dilated (between 1-1.5 times the control airway caliber), and 2 when very dilated (more than 1.5 times the control airway caliber). In addition, the following histological features were analyzed: areas of atelectasis, interstitial and/or alveolar edema, inflammatory infiltration, interlobular septa ruptures, and desquamation of bronchiolar epithelium. Each pathological feature was evaluated as 1 when present and 0 when absent. A score of pulmonary damage, which was considered negative=0, slight=0-1, moderate=2-3, and severe≧4, is achieved by adding the scores up.

Statistical Analysis.

Time-dependent changes were analyzed with a one-way analysis of variance for repeated measures. Time-course evolution between the different groups was compared using a two-way analysis of variance for repeated measures and one grouping factor (i.e., "time" and "treatment"). Intra group comparisons in the different groups between different treatment conditions are tested with paired Student's t-tests. Results were expressed as mean±standard deviation, and a p value<0.05 was considered significant.

Results.

Eighteen animals were randomized to receive 200 mg/kg of natural surfactant (n=6), 200 mg/kg of surfactant plus 400 µg/kg of beclometasone dipropionate (n=6), and 200 mg/kg of surfactant plus 800 µg/kg of beclometasone dipropionate (n=6).

Gas Exchange.

Table 1 reports changes of pH and blood gas analysis in the study groups. In all groups a significant increase of pH at $T_1$, $T_2$, $T_4$, and $T_6$ in comparison with baseline values is observed; $pCO_2$ does not vary in the surfactant group, while decreases significantly in the surfactant plus beclometasone dipropionate groups at $T_1$, $T_2$, $T_4$, and $T_6$; $pO_2$ is similar in the groups at each time; BE exhibits a trend toward a reduction in every group, but statistical changes are transient and poor relevant.

MAP and Lung Mechanics.

Table 2 shows changes of MAP, TV, Cdyn, and Raw. MAP significantly decreases in the group treated with surfactant plus 800 µg/kg of beclometasone dipropionate at $T_4$, and $T_6$, and is lower than in other groups; TV and Raw decrease from baseline in all the groups, while Cdyn does not change.

Oxidative Stress Assays.

Table 3 details changes of TH, AOPP, and NPBI. TH is lower at $T_6$ in the group treated with surfactant plus 400 µg/kg of beclometasone dipropionate than in the surfactant group, and at $T_4$ and $T_6$ in the group treated with surfactant plus 800 µg/kg of beclometasone dipropionate than in the other groups; the AOPP increases at $T_1$ and then dropped at $T_2$, $T_4$, and $T_6$ in all the groups, but at $T_6$ its value is lower in the group treated with surfactant plus 800 µg/kg of beclometasone dipropionate than in the other groups. NPBI is found in all groups and its concentration does not change and does not vary between the groups.

Macro-Microscopic Features.

On gross examination, the lungs of animals treated with surfactant plus 800 µg/kg of beclometasone dipropionate exhibit a trend toward a better aeration than the other groups. On microscopic examination, distal airways appear more collapsed in the surfactant group than in the surfactant plus 400 or 800 µg/kg of beclometasone dipropionate groups. Moreover, areas of atelectasis, some alveoli containing macrophages, and some interlobular septa leakages are observed. The overall pulmonary damage score is lower in the surfactant plus 400 µg/kg of beclometasone dipropionate group (1.8±0.7) and in the surfactant plus 800 µg/kg of beclometasone dipropionate group (1.8±0.3) than in the surfactant group (2.4±0.6), but the difference is not statistically significant.

Discussion.

The results demonstrate that the treatment with poractant alfa combined with beclometasone dipropionate is effective in decreasing the lung oxidative stress in preterm lambs with respiratory failure. In fact, it has been observed that the intra-tracheal instillation of surfactant plus 800 µg/kg of beclometasone dipropionate is followed by lower levels in bronchial aspirate samples of TH at $T_4$ and $T_6$, and AOPP at $T_6$ compared to the other groups; the intra-tracheal instillation of surfactant plus 400 µg/kg of beclometasone dipropionate is followed by a decrease of TH at $T_6$ compared to the surfactant group, while the instillation of surfactant alone has no effect on the concentration of oxidative stress markers. These results are relevant because TH represents a measure of overall oxidative stress, given that it is the intermediate oxidative product of lipids, peptides, and amino acids, while simultaneous determination of AOPP provides information regarding another aspect of protein involvement in free radical reactions, namely oxidized proteins that have lost their oxidant properties.

Differently, the concentration of NPBI does not vary in study groups. However, as previously reported, the NPBI values can be unrelated to concentration changes of other markers of oxidative stress likely because they are formed also from other sources.

Moreover, as far as lung compliance is concerned, it has been observed that surfactant treatment is followed by a sustained improvement of TV and Raw, while Cdyn is unchanged. However, surprisingly, beclometasone dipropionate at a dose of 800 µg/kg synergistically lowers the mean airway pressure (MAP) needed to obtain the same value of TV in comparison to the group treated with surfactant plus beclometasone dipropionate at a dose of 400 mg/kg and surfactant alone.

Therefore, the effect of intratracheal beclometasone dipropionate at a dose of 800 µg/kg is not limited to a decrease of lung oxidative stress but is also consistent with an improvement of the lung mechanics, and hence the respiratory function of animals.

In agreement with other findings, histological examination shows a trend toward a reduction of morphologic lung damage in the groups which received surfactant plus beclometasone dipropionate.

TABLE 1

Changes of blood gas analysis in preterm lambs treated with surfactant plus 400 μg/kg of beclometasone dipropionate (BDP), or surfactant plus 800 μg/kg of beclometasone dipropionate (BDP). Mean ± SDs.

|  | Surfactant | Surfactant + BDP 400 μg | Surfactant + BDP 800 μg |
|---|---|---|---|
| pH: | | | |
| Baseline | 6.93 ± 0.09* | 6.90 ± 0.09** | 7.02 ± 0.07** |
| $T_1$ | 7.11 ± 0.25 | 7.26 ± 0.16 | 7.34 ± 0.11 |
| $T_2$ | 7.23 ± 0.21 | 7.32 ± 0.17 | 7.36 ± 0.05 |
| $T_4$ | 7.23 ± 0.18 | 7.32 ± 0.09 | 7.36 ± 0.08 |
| $T_6$ | 7.19 ± 0.17 | 7.36 ± 0.09 | 7.37 ± 0.10° |
| pCO₂: | | | |
| Baseline | 86 ± 25 | 109 ± 12** | 93 ± 20*** |
| $T_1$ | 62 ± 26 | 49 ± 26 | 47 ± 16 |
| $T_2$ | 70 ± 40 | 46 ± 18 | 43 ± 14 |
| $T_4$ | 63 ± 29 | 50 ± 13 | 42 ± 7 |
| $T_6$ | 64 ± 38 | 47 ± 17 | 38 ± 7 |
| pO₂: | | | |
| Baseline | 96 ± 113 | 71 ± 54 | 106 ± 133 |
| $T_1$ | 150 ± 158 | 164 ± 84 | 147 ± 110 |
| $T_2$ | 160 ± 165 | 155 ± 114 | 100 ± 134 |
| $T_4$ | 147 ± 132 | 131 ± 93 | 151 ± 139 |
| $T_6$ | 134 ± 177 | 95 ± 100 | 123 ± 146 |
| BE: | | | |
| Baseline | −11.7 ± 6.7^ | −5.5 ± 6.6 | −6.6 ± 5.6 |
| $T_1$ | −6.1 ± 6.6 | −6.8 ± 6.0 | −1.3 ± 2.1 |
| $T_2$ | −4.1 ± 4.4 | −0.32 ± 5.1 | −1.1 ± 2.9 |
| $T_4$ | −3.9 ± 0.7 | −1.6 ± 1.9^^ | −2.1 ± 3.5 |
| $T_6$ | −5.3 ± 4.7 | −2.1 ± 1.9 | −3.4 ± 4.8 |

*p = 0.009 vs. 2 h; p = 0.004 vs. 4 h. p = 0.008 vs. 6 h
**p < 0.0001 vs. 1, 2, 4, 6 h. p = 0.001 vs. 1 h, p < 0.0001 vs. 2, 4 h.
°p = 0.049 vs. Surfactant
^p = 0.018 vs 4 h;
^^0.019 vs. Surfactant;

TABLE 2

Changes of mean airway pressure (MAP) and lung mechanics in preterm lambs treated with surfactant, surfactant plus 400 μg/kg of beclometasone dipropionate (BDP), or surfactant plus 800 μg/kg of beclometasone dipropionate (BDP). Mean ± SDs.

|  | Surfactant | Surfactant + BDP 400 | Surfactant + BDP 800 |
|---|---|---|---|
| MAP | | | |
| Baseline | 15.2 ± 1.0 | 15.8 ± 1.2 | 16.2 ± 1.3 |
| $T_1$ | 16.0 ± 2.3 | 16.2 ± 1.7 | 16.2 ± 1.6 |
| $T_2$ | 15.6 ± 1.9 | 16.0 ± 1.7 | 15.8 ± 2.6 |
| $T_4$ | 15.5 ± 1.3 | 15.2 ± 3.2 | 11.0 ± 2.3* |
| $T_6$ | 15.7 ± 2.6 | 15.5 ± 3.0 | 11.8 ± 2.5** |
| TV (ml/kg) | | | |
| Baseline | 3.9 ± 1.7# | 4.1 ± 1.0# | 4.1 ± 1.9# |
| $T_1$ | 11.3 ± 4.2 | 11.8 ± 4.2 | 11.5 ± 3.2 |
| $T_2$ | 10.4 ± 3.0 | 11.7 ± 4.4 | 11.2 ± 1.3 |
| $T_4$ | 10.4 ± 3.1 | 12.2 ± 8.3 | 11.6 ± 1 |
| $T_6$ | 11.3 ± 4.5 | 11.9 ± 2.2 | 11.4 ± 2.1 |
| Cdyn (/kg) | | | |
| Baseline | 0.4 ± 0.1 | 0.4 ± 0.5 | 0.5 ± 0.8 |
| $T_1$ | 0.4 ± 0.1 | 0.4 ± 0.1 | 0.4 ± 0.1 |
| $T_2$ | 0.4 ± 0.1 | 0.4 ± 0.1 | 0.5 ± 0.3 |
| $T_4$ | 0.5 ± 0.1 | 0.5 ± 0.2 | 0.6 ± 0.2 |
| $T_6$ | 0.6 ± 0.3 | 0.5 ± 0.1 | 0.5 ± 0.1 |
| Raw | | | |
| Baseline | 283 ± 73^ | 295 ± 13^^ | 308 ± 13^^^ |
| $T_1$ | 235 ± 25 | 219 ± 41 | 248 ± 47 |
| $T_2$ | 214 ± 24 | 225 ± 20 | 237 ± 43 |
| $T_4$ | 195 ± 71 | 225 ± 11 | 208 ± 13 |
| $T_6$ | 185 ± 43 | 208 ± 44 | 231 ± 41 |

*p < 0.0001 vs. baseline; p = 0.003 vs. $T_1$, p = 0.022 vs. $T_2$, p = 0.002 vs. surfactant, p = 0.026 vs. surfactant + BDP 400
**p = 0.003 vs. baseline; p = 0.005 vs. $T_1$, p = 0.022 vs $T_2$; p = 0.024 vs surfactant, p = 0.043 vs. surfactant + BDP 400
p < 0.0001 vs. $T_1$, $T_2$, $T_4$, $T_6$
^p = 0.018 vs $T_6$
^^p = 0.001 vs 1 h, <0.0001 vs. $T_1$, $T_2$, $T_4$, $T_6$
^^^p = 0.013 vs. $T_1$, p = 0.003 vs. $T_2$; p < 0.0001 vs $T_4$; p = 0.003 vs. $T_6$

TABLE 3

Changes of TH, AOPP, and NPBI in preterm lambs treated with surfactant, surfactant plus 400 μg/kg of beclometasone dipropionate (BDP), or surfactant plus 800 μg/kg of beclometasone dipropionate (BDP). Mean ± SDs.

|  | Baseline | $T_1$ | $T_2$ | $T_4$ | $T_6$ |
|---|---|---|---|---|---|
| TH (Carr Unit) | | | | | |
| Surfactant | 73.6 ± 15.4 | 85.5 ± 18.1 | 86.1 ± 35.1 | 94.2 ± 35.5 | 93.4 ± 20.5 |
| Surfactant + BDP 400 | 42.9 ± 18.6 | 73.6 ± 27.9 | 61.7 ± 29.6 | 65.7 ± 30.1 | 52.7 ± 22.2^ |
| Surfactant + BDP 800 | 77.8 ± 61.3 | 50.1 ± 61.1 | 95.1 ± 61.1 | 57.6 ± 23.2* | 58.2 ± 26.0** |
| AOPP (μmol/L) | | | | | |
| Surfactant | 2.1 ± 1.8# | 25.9 ± 9.2 | 13.6 ± 8.3 | 18.5 ± 11.6 | 18.7 ± 9.7 |
| Surfactant + BDP 400 | 4.6 ± 2.2## | 36.9 ± 24.7 | 17.3 ± 7.0 | 15.3 ± 8.1 | 11.5 ± 10.9 |
| Surfactant + BDP 800 | 1.9 ± 0.6### | 16.3 ± 9.7 | 12.2 ± 11.6 | 8.2 ± 5.7 | 7.2 ± 2.8° |
| NPBI | | | | | |
| Surfactant | 0.9 ± 2.0 | 1.6 ± 1.6 | 0.4 ± 0.7 | 1.4 ± 1.1 | 0.3 ± 0.6 |
| Surfactant + BDP 400 | 0.3 ± 0.4 | 2.7 ± 2.3 | 1.2 ± 2.3 | 0.8 ± 0.8 | 0.5 ± 0.8 |
| Surfactant + BDP 800 | 0.3 ± 0.1 | 0.3 ± 0.6 | 0.6 ± 1.0 | 0.7 ± 1.5 | 0.0 ± 0.0 |

^p = 0.008 vs. surfactant;
*p = 0.060 vs. surfactant
**p = 0.026 vs. surfactant.
p < 0.0001 vs. $T_1$, $T_4$, $T_6$; p = 0.008 vs. $T_2$;
p = 0.010 vs. $T_1$; p = 0.002 vs. $T_2$; p = 0.011 vs. $T_4$; ###p = 0.005 vs. $T_1$; p = 0.023 vs. $T_4$; p = 0.001 vs. $T_6$.
°p = 0.019 vs. surfactant.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A composition, comprising poractant alfa and beclometasone dipropionate,
   wherein said poractant alfa and beclometasone dipropionate are present in relative amounts suitable for administering said poractant alfa at a dose of about 100 to about 200 mg/kg and said beclometasone dipropionate at a dose of about 0.6 to about 0.8 mg/kg.

2. A composition according to claim 1, wherein said poractant alfa and said beclometasone dipropionate are present in relative amounts suitable for administering said poractant alfa in a dose of about 100 to about 200 mg/kg and said beclometasone dipropionate in a dose of about 0.8 mq/kg.

3. A composition according to claim 1, wherein said poractant alfa and said beclometasone dipropionate are present in relative amounts suitable for administering said poractant alfa at a dose of about 200 mg/kg and said beclometasone dipropionate in a dose of about 0.8 mg/kg.

4. A composition according to claim 1, which is in a form suitable for inhalation or intratracheal administration.

5. A composition according to claim 1, which is in a form of a sterile suspension in a buffered physiological saline aqueous solution.

6. A method for prevention of bronchopulmonary dysplasia, comprising administering poractant alfa at a dose of about 100 to about 200 mg/kg and beclometasone dipropionate at a dose of about 0.6 to about 0.8 mq/kg to a subject in need thereof.

7. A method according to claim 6, wherein said poractant alfa is administered in a dose of about 200 mg/kg.

8. A method according to claim 6, wherein said beclometasone dipropionate is administered in a dose of about 0.6 mg/kg.

9. A method according to claim 6, wherein said beclometasone dipropionate is administered in a dose of about 0.8 mg/kg.

10. A method according to claim 6, wherein said poractant alfa is administered in a dose of about 200 mg/kg and said beclometasone dipropionate is administered in a dose of about 0.6 mg/kg.

11. A method according to claim 6, wherein said poractant alfa is administered in a dose of about 200 mg/kg and said beclometasone dipropionate is administered in a dose of about 0.8 mg/kg.

12. A method for lowering a marker of pulmonary oxidative stress, comprising administering poractant alfa at a dose of about 100 to about 200 mg/kg and beclometasone dipropionate at a dose of about 0.6 to about 0.8 mg/kg to a subject in need thereof.

13. A method according to claim 12, wherein said poractant alfa is administered in a dose of about 200 mg/kg.

14. A method according to claim 12, wherein said beclometasone dipropionate is administered in a dose of about 0.6 mg/kg.

15. A method according to claim 12, wherein said beclometasone dipropionate is administered in a dose of about0.8 mg/kg.

16. A method according to claim 12, wherein said poractant alfa is administered in a dose of about 200 mg/kg and said beclometasone dipropionate is administered in a dose of about 0.6 mg/kg.

17. A method according to claim 13, wherein said poractant alfa is administered in a dose of about 200 mg/kg and said beclometasone dipropionate is administered in a dose of about 0.8 mg/kg.

18. A kit, comprising:
    (a) poractant alfa at a dose of about 100 and about 200 mg/kg and a pharmaceutically acceptable carrier or diluent in a first unit dosage form;
    (b) beclometasone dipropionate at a dose of about 0.6 to about 0.8 mg/kg and a pharmaceutically acceptable carrier or diluent in a second unit dosage form; and
    (c) a container which contains said first and second dosage forms.

19. A kit according to claim 18, wherein the dose of poractant alfa is about 200 mg/kg.

20. A kit according to claim 18, wherein said first unit dosage form is a single-use vial filled with about 2.5 ml of a sterile formulation of about 80 mg/ml poractant alfa suspended in a buffered physiological saline aqueous solution, while the second unit dosage form is a single-use vial filled with about 2 ml of a sterile formulation of micronised beclometasone dipropionate suspended in an aqueous solution comprising polysorbate (Tween) 20, sorbitan monolaurate, and sodium chloride.

\* \* \* \* \*